United States Patent [19]

Ware

[11] 4,243,042
[45] Jan. 6, 1981

[54] ENCLOSURE SYSTEM FOR BODY IMPLANTABLE ELECTRICAL SYSTEMS

[75] Inventor: Lyle A. Ware, Bloomington, Minn.

[73] Assignee: Medtronic, Inc., Minneapolis, Minn.

[21] Appl. No.: 7,307

[22] Filed: Jan. 29, 1979

Related U.S. Application Data

[63] Continuation of Ser. No. 793,638, May 4, 1977, abandoned.

[51] Int. Cl.³ .............................................. A61N 1/02
[52] U.S. Cl. .................................................. 128/419 P
[58] Field of Search ........ 128/419 P, 419 PG, 419 PS

[56] References Cited

U.S. PATENT DOCUMENTS

| | | | |
|---|---|---|---|
| 3,357,434 | 12/1967 | Abell | 128/419 P |
| 3,823,037 | 7/1974 | Cairns et al. | 128/419 PS |
| 3,866,616 | 2/1975 | Purdy et al. | 128/419 PS |
| 3,888,620 | 6/1975 | Fischell | 128/419 P |
| 3,918,460 | 11/1975 | King et al. | 128/419 P |
| 3,957,056 | 5/1976 | Comben et al. | 128/419 P |
| 4,041,956 | 8/1977 | Purdy et al. | 128/419 P |

*Primary Examiner*—William E. Kamm
*Attorney, Agent, or Firm*—Schroeder, Siegfried, Ryan, Vidas, Steffey & Arrett

[57] ABSTRACT

An improved body implantable electrical stimulator assembly of the type having interconnected electrical components housed within a preformed enclosure. A cup is provided in which the components are finally assembled, the cup being configured to fit within the enclosure. Preferably, the enclosure is formed of a plurality of members at least one of which has a main wall and a side wall joined at a radius. The cup is similarly formed of a main wall and a side wall, the main wall being generally coextensive with at least a major portion of the enclosure member main wall. The cup engages the enclosure in a manner such that its movement within the enclosure is limited. Movement of the components within the cup is restrained.

10 Claims, 12 Drawing Figures

ENCLOSURE SYSTEM FOR BODY IMPLANTABLE ELECTRICAL SYSTEMS

This is a continuation of application Ser. No. 793,638, filed May 4, 1977, now abandoned.

BACKGROUND OF THE INVENTION

Body implantable electrical stimulators are well known to the prior art, the most common being the cardiac pacemaker. The electrical components forming such stimulators have been housed in a matrix of molded material which supports the components and shields them from the body environment. More recently, the electrical components forming the stimulator have been housed within a rigid enclosure formed of a plurality of preformed members which are typically welded together to complete the enclosure.

Some of the problems attending the use of a preformed rigid enclosure for a body implantable electrical stimulator are the need to electrically insulate the components from the enclosure, isolation of the components against shock and vibration, and securement of the components within the enclosure. These problems have been addressed by molding the assembled electrical components within a matrix of material to support the components relative to each other and provide an isolation between the components and the enclosure, with the molded matrix then being secured to the enclosure, as by an adhesive.

SUMMARY OF THE INVENTION

The present invention provides a cup in which the components of a body implantable electrical stimulator may be assembled, the cup being configured to fit within a preformed electrical stimulator enclosure. The components are secured within the cup, and the cup is provided with means for mechanically limiting its movement within the enclosure. Thus, the necessity of molding the assembled components is eliminated as is the need to secure the component mold within the enclosure. The components may be secured within the cup by an encapsulating material which substantially fills the cup, or by elements which engage one or more components to mechanically maintain them in position. In a preferred embodiment, the enclosure is formed of a plurality of members at least one of which has a main wall and a side wall joined at a radius. The cup is formed of a main wall and a side wall, the cup main wall being generally coextensive with at least a major portion of the enclosure member main wall with the cup side wall encircling the components. The cup is further provided with means engaging the enclosure member radius to limit movement of the cup within the enclosure. The cup side wall may be provided with an antenna coil form when an antenna is required by the stimulator in question.

DETAILED DESCRIPTION OF THE DRAWINGS

Figure 1:
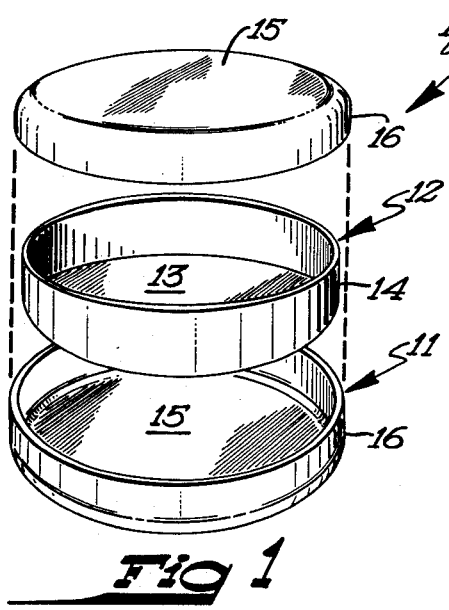
FIG. 1 is an exploded view illustrating a two member preformed enclosure and the cup of the present invention.

FIG. 1 is an exploded view illustrating the concept of the present invention. An electrical stimulator enclosure is formed of first and second preformed members 10 and 11 which have generally circular main walls 15 and cylindrical side walls 16. The enclosure is formed by placing the side walls 16 together and joining them, as by welding. Enclosures of this type are known to the prior art, an example being that disclosed in copending application Ser. No. 659,650, filed Feb. 20, 1976, now U.S. Pat. No. 4,057,068 which is co-owned with the present application, and is incorporated herein by reference. As illustrated in FIG. 1, members 10 and 11 are identical. Within the context of the present invention, however, only one of the members 10 and 11 need have a main wall and a side wall. The members 10 and 11 may be any desired shape, but preferably, have a generally cylindrical side wall. Within the cylindrical side wall, provision may be made for electrical communication with components housed within the enclosure in a manner similar to that of the incorporated patent application, for example.

A cup 12 is illustrated in FIG. 1 having a main wall 13 and side wall 14, the cup being configured to fit within and substantially fill the enclosure formed by the members 10 and 11. The components forming the electrical stimulator may be assembled within the cup 12, the cup 12 then being placed within the member 11, the member 10 being placed over the cup and into engagement with the member 11, members 10 and 11 then being secured to each other, as by welding, for example. The cup 12, as illustrated in FIG. 1, greatly facilitates assembly of the components forming the electrical stimulator, and eliminates the otherwise required step of molding the assembled components. Additionally, the cup assists in the electrical insulation of the components from the enclosure and serves to isolate the components from shock and vibration. In a preferred embodiment, to be discussed below, the cup side wall may also be provided with an antenna coil form when the use of an antenna is required.

In addition to assisting assembly of the stimulator components and insulating and isolating them from the enclosure, the cup which forms a portion of the present invention also serves to secure the components in position within the enclosure. The components are secured within the cup in a manner to be described more fully below. Additionally, the cup is provided with means for mechanically limiting its movement within the enclosure, thereby limiting movement of the components relative to the enclosure.

Figure 2:
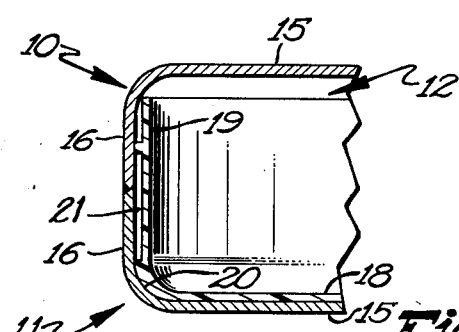
FIG. 2 illustrates a cross-section of a preferred embodiment of the cup of the present invention and its cooperation with enclosure members of FIG. 1.

A preferred system for limiting the movement of the cup relative to the enclosure is illustrated in FIG. 2 which is a cross-section of an assembled enclosure of the type illustrated in FIG. 1, with a preferred cup embodiment positioned therein. As illustrated, members 10 and 11 each have a main wall 15 which is generally circular (see FIG. 1), and side wall 16, the main wall 15 and side wall 16 being joined to each other at a radius 17. The abutment of the side wall 16 of members 10 and 11 may be joined together as by welding, for example. Within the enclosure formed by the members 10 and 11, there is positioned a cup having a main wall 18 and a side wall 19. The cup is provided with a radius 20 at the outside junction of the main wall 18 and side wall 19, which is in substantial conformity with the radius 17 of the member 11. When urged into position, the radius 20 engages the radius 17 to mechanically prevent movement of the cup within the enclosure formed by the members 10 and 11, and, through friction, restricts rotation of the cup relative to the enclosure. Radius 20 is urged against the radius 17 by a force imparted to the cup, or its contents, by the member 10 when the side walls 16 are in abutment and is maintained in that position for so long as the enclosure remains closed. Preferably, the cup is made of a resilient or flexible material capable of conforming the radius 20 to the radius 17 under the influence of the force imparted to the cup via the member 10, while resisting deformation under that force which might relieve the engagement between the radius 20 and the radius 17. Polypropylene has been found to be a suitable material for the embodiment illustrated in FIG. 2, as well as the other embodiments illustrated herein. Other materials having the required properties may also be used, Nylon, for example. The outer surface of the side wall 19 may be provided with a recess 21 above the radius 20 and running around its periphery to act as an antenna coil form. That is, an antenna may be wound or otherwise constructed within the recess 21 when the presence of an antenna is necessary to the operation of the electrical stimulator in question.

Figure 3:
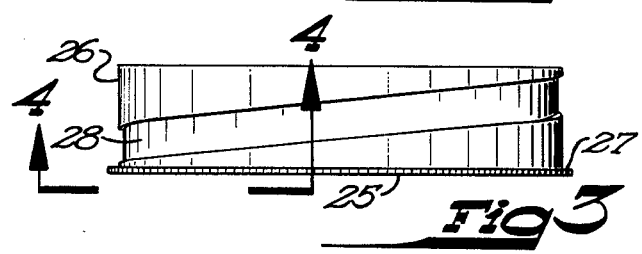
FIG. 3 illustrates another preferred embodiment of the cup of the present invention.
Figure 4:
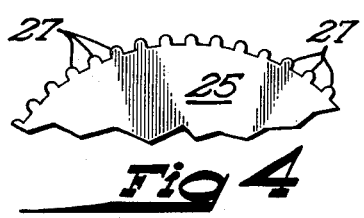
FIG. 4 is a view taken along the line 4—4 in FIG. 3.

Referring now to FIG. 3, there is illustrated a side view of another preferred embodiment of the cup forming a part of the present invention. The cup of FIG. 3 has a main wall 25 and a side wall 26. Extending from the junction of the main wall 25 and side wall 26 are a plurality of finger-like members 27 (see FIG. 4) which function in a manner similar to the radius 20 in the embodiment of FIG. 2 to limit movement of the cup within the enclosure. The outer surface of the side wall 26 may be provided with a recess 28 to function as an antenna coil form when appropriate. The recess 28 may be equidistant from the main wall 25. As illustrated, however, the recess 28 is skewed relative to the main wall 25. That is, a plane through the recess 28 is skewed relative to the plane of the main wall 25. In this manner, an antenna within the recess 28 will be closer to the main wall of enclosure member 10 in one location and closer to the main wall of enclosure member 11 in another location so as to increase its sensitivity beyond that which might otherwise be possible if the recess 28 were equidistant in all places from the main wall 25 and, thus, the main walls of the members 10 and 11. Additionally, the skewing of the recess 28 provides a larger antenna coil diameter than would be the case if the recess 28 were equidistant from the main wall 25.

Figure 5:
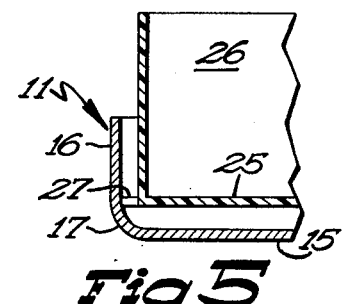
FIGS. 5 and 6 illustrate the cooperation of the embodiment of FIGS. 3 and 4 with an enclosure member.
Figure 6:
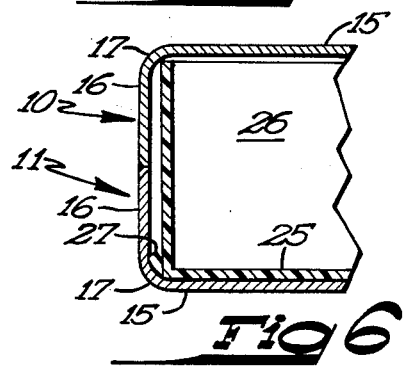

Referring now to FIGS. 5 and 6, the cooperation of the finger members 27 with the radius 17 of one of the enclosure members is illustrated. The cup of FIG. 3 is positioned within the enclosure member 11, the members 27 engage the inner surface of the radius 17, and maintain the main wall 25 of the cup spaced from the main wall 15 of the enclosure member 11. A force is imparted to the cup, or its contents, by the enclosure member 10 when the side wall 16 of the enclosure members 10 and 11 are in abutment. This force causes the members 27 to deform and resiliently engage the inner surface of the radius 17 (see FIG. 6) thereby limiting both lateral and rotational movement of the cup within the enclosure. The resilient nature of the cup material causes the members 27 to continually engage the inner surface of the radius 17 and maintain the motion limitation provided thereby.

Figure 7:
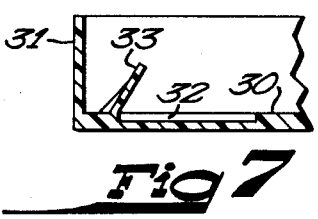
FIGS. 7 and 8 illustrate a preferred embodiment of the present invention.
Figure 8:
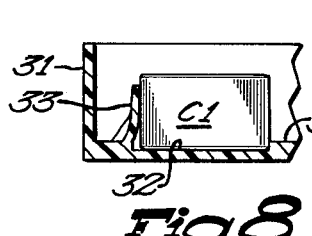

To this point, there has been described preferred embodiments of a cup member in which the electrical components that embody the implantable stimulator may be assembled and which cooperates with the members forming an enclosure for the stimulator to limit movement of the cup member within the enclosure. FIGS. 7 and 8 illustrate a preferred embodiment for restraining the movement of at least some of the components forming the electrical stimulator. FIGS. 7 and 8 show a partial cross-section of a cup member having a main wall 30 and a side wall 31. The junction of the main wall 30 and side wall 31 may be provided with a radius 20 or members 27 as described above with reference to FIGS. 2-6. The inner surface of the main wall 30 is provided with a recess 32 of a size which will accept one of the stimulator electrical components. Extending from the main wall 30 and over the recess 32 is a spring tab 33 which may be unitary with the main wall 30. An electrical component C1 (see FIG. 8) may be inserted within the recess by engaging it against the spring tab 33 to push it out of blocking relation relative to the recess 32 and putting the component C1 within the recess 32. Spring tab 33 will then engage the component C1 and urge it against the recess wall in a manner which will maintain the component C1 within the recess. Electrical components of the type employed within a body implantable electrical stimulator are manufactured to nominal dimensions within a stated tolerance range. The recess 32 is made large enough to accept all components within the given tolerance range and the spring tab 33 will engage all components within the tolerance range to urge them against the wall of the recess 32. Therefore, not only does the cooperation between the recess 32 and spring tab 33 maintain a component in position within the cup, the cooperation of those elements accomodates parts of varying dimensions within a known tolerance range (tolerance accumulation). One or more recesses 32 and spring tabs 33 may be provided within the main wall 30 to accomodate one or more major components of the stimulator to secure and maintain them in position within the cup, the cup being limited in its movement within the enclosure formed by members 10 and 11, as stated above. Therefore, components secured within the cup as illustrated with reference to component C1 are secured against movement within the enclosure as well.

Figure 9:
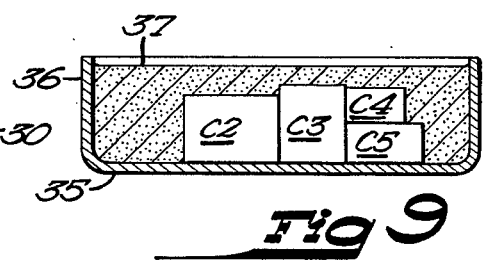
FIG. 9 illustrates still another preferred embodiment of the present invention.

Referring now to FIG. 9, there is shown an alternative embodiment for securing the assembled electrical components within a cup. The cup is formed of a main wall 35 and a side wall 36 whose junction may be provided with a radius 20 or finger members 27 as described above with reference to FIGS. 2-6. Components C2-C5 are assembled within the cup and the cup is substantially filled with an encapsulating material 37 which forms a matrix surrounding the components C2-C5 to hold them in position relative to each other and secure them within the cup. The cup is then positioned within the enclosure formed by members 10 and 11 with the components C2–C5 being maintained in position relative to the cup and the enclosure. The encapsulating material 37 may be silicone rubber or another similar material suitable for use in a body implantable device.

Figure 10:
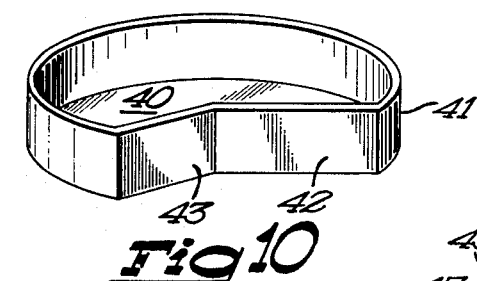
FIG. 10 illustrates an enclosure member to which the cup of the present invention may be adapted.
Figure 11:
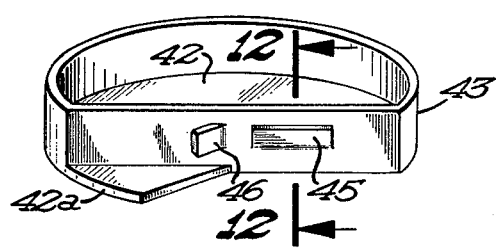
FIG. 11 illustrates an adaptation of the cup of the present invention to the enclosure member of FIG. 10.
Figure 12:
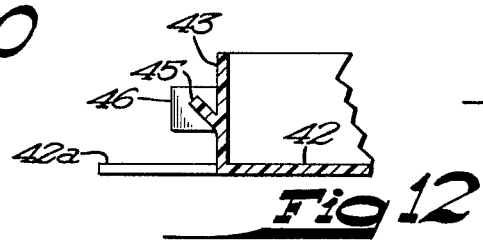
FIG. 12 illustrates a cross-section taken along line 12—12 in FIG. 11.

As discussed above, the incorporated patent makes provision for electrical communication with the enclosed electrical stimulator. In the incorporated patent, this is accomplished through the use of a recess within one of the side walls of the enclosure member. A similar but alternative enclosure member is illustrated in FIG. 10 which has a main wall 40 and a side wall 41 joined at a radius such as that illustrated in FIGS. 2, 5 and 6. The side wall 41 is generally cylindrical, having platforms 42 and 43 through which electrical communication may be made. The enclosure may be completed with a plate welded to the end of the side wall 41 or with a complimentary member having a side wall corresponding to the side wall 41 of the same or a different height than the side wall 41. A cup for use in an enclosure formed at least in part by a member such as that illustrated in FIG. 10 is illustrated in FIG. 11. The cup of FIG. 11 includes a main wall 42 which is generally coextensive with at least a major portion of the main wall 40 of the member of FIG. 10. A side wall 43 extends from the main wall 42 and encircles an area in which the electrical components are to be assembled. The main wall contains a portion 42a which extends beyond that area encircled by the side wall 43. The junction between the main wall 42 and side wall 43 may be provided with a radius 20 or finger members 27 as illustrated in FIGS. 2–6. Preferably, the finger members 27 of FIGS. 3–6 extend from the junction of the main wall 42 and side wall 43 as well as from the main wall portion 42a to engage the radius between the main wall 40 and side wall 41 of the enclosure member of FIG. 10 as described above. Additionally spring tabs 45 and 46 may be provided to engage the platforms 42 and 43, respectively, the spring tab 45 urging the cup member away from the platform 42 while the spring tab 46 engages the platform 43 to assist in preventing rotation of the cup member within the enclosure member. The spring tab 46 may be used in combination with the main wall portion 42a, or as an alternative to it for the purpose of preventing rotation. The spring tabs 45 and 46 facilitate and enhance the engagement between the radius 20 or finger members 27 with the inner surface of radius 17, as discussed above with reference to FIGS. 2–6. The major functions of the present invention, however, may be accomplished through the use of the radius 20 and/or finger members 27 without the use of the spring tabs. Within the context of the incorporated patent, the spring tab 46 may be angled to cooperate with the reverse side of platform 31 illustrated in FIGS. 5–7 of the incorporated patent for the purpose essentially as described herein, with or without the main wall portion 42a.

Obviously many modifications and variations of the present invention are possible in light of the above teachings. For example, the configuration of the main wall and side wall of the cup member described herein may be configured to be accomodated within any enclosure formed of two or more members whether generally cylindrical or otherwise. The cup member need not totally fill the enclosure, but should preferably substantially fill the enclosure to minimize wasted space within the enclosure and maximize the contact between the enclosure member radius and the cup member radius engaging means. In addition, the use of spring tabs such as 45 and 46 may or may not be necessary within the context of a particular enclosure configuration, that decision being within the skill of one ordinarily skilled in the art having reference to the teachings herein. Accordingly, within the scope of the appended claims, the invention may be practiced other than as specifically described.

What is claimed is:

1. In a body implantable electrical stimulator of the type having interconnected electrical components housed within a preformed enclosure, the enclosure having a plurality of members at least one of which has a main wall and a side wall joined at a radius, the improvement which comprises cup means formed of a main wall and a side wall, said cup main wall being generally coextensive with at least a major portion of said enclosure member main wall and said cup means side wall encircling said components, said cup means further comprising means engaging said enclosure member radius for mechanically limiting movement of said cup means within said enclosure.

2. The body implantable stimulator of claim 1 wherein said radius engaging means comprises a plurality of extending members resiliently engaging said enclosure member radius.

3. The body implantable stimulator of claim 1 wherein said radius engaging means comprises radius means joining said cup means main and side walls and resiliently urged into engagement with said enclosure member side walls.

4. The body implantable stimulator of claim 1 further comprising means for maintaining said components in position within said cup means.

5. The body implantable stimulator of claim 4 wherein said component position maintaining means comprises an encapsulating material substantially filling said cup means.

6. The body implantable stimulator of claim 4 wherein said component position maintaining means comprises tab means engaging at least some of said components.

7. The body implantable stimulator of claim 4 wherein the inner surface of said cup means is provided with at least one recess configured to accept one of said components, said component position maintaining means comprising means unitary with said cup means resiliently engaging said one component to maintain it within a recess while allowing for differences in size in the component within said recess.

8. The body implantable stimulator of claim 1 wherein said cup means further comprises a side wall provided with antenna coil form means.

9. The body implantable stimulator of claim 8 wherein said antenna coil form means lies generally within a plane which is skewed relative to said cup means main wall.

10. In a body implantable electrical stimulator of the type having interconnected electrical components housed within a preformed enclosure, the improvement which comprises cup means configured to fit within said enclosure and having a main wall and a side wall, said side wall being provided with an antenna coil form which lies generally within a plane which is skewed relative to said main wall so as to increase the sensitivity of an antenna within said coil form.

* * * * *